(12) United States Patent
Oda

(10) Patent No.: US 8,413,079 B2
(45) Date of Patent: Apr. 2, 2013

(54) DISPLAY PROCESSING APPARATUS FOR IMAGE INFORMATION

(75) Inventor: Yasuharu Oda, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 948 days.

(21) Appl. No.: 12/145,887

(22) Filed: Jun. 25, 2008

(65) Prior Publication Data

US 2009/0003732 A1   Jan. 1, 2009

(30) Foreign Application Priority Data

Jun. 27, 2007   (JP) ................. 2007-169684

(51) Int. Cl.
*G06K 9/60* (2006.01)
(52) U.S. Cl. .......... 715/866; 382/305; 382/128; 348/65; 600/476
(58) Field of Classification Search .......... 715/866, 715/771; 382/128; 600/476
See application file for complete search history.

(56) References Cited

U.S. PATENT DOCUMENTS

| | | | |
|---|---|---|---|
| 5,224,481 A * | 7/1993 | Ishihara et al. | 600/443 |
| 6,609,135 B1 * | 8/2003 | Omori et al. | 1/1 |
| 2002/0177779 A1 | 11/2002 | Adler et al. | |
| 2004/0249291 A1 * | 12/2004 | Honda et al. | 600/476 |
| 2005/0094017 A1 | 5/2005 | Hirakawa | |
| 2006/0160054 A1 * | 7/2006 | Onishi et al. | 434/322 |
| 2008/0031503 A1 * | 2/2008 | Kanada et al. | 382/128 |
| 2008/0201657 A1 * | 8/2008 | Archer et al. | 715/771 |
| 2009/0019381 A1 | 1/2009 | Kimoto | |
| 2009/0080734 A1 * | 3/2009 | Moriya et al. | 382/128 |

FOREIGN PATENT DOCUMENTS

| | | |
|---|---|---|
| CN | 1777391 A | 5/2006 |
| EP | 1 922 977 A1 | 5/2008 |

(Continued)

OTHER PUBLICATIONS

International Search Report dated Aug. 26, 2008.

(Continued)

*Primary Examiner* — Matt Kim
*Assistant Examiner* — Tuan S Nguyen
(74) *Attorney, Agent, or Firm* — Scully, Scott, Murphy & Presser, P.C.

(57) ABSTRACT

On a display processing apparatus, on a case data selection screen, display call buttons for respectively instructing the display of the case data selection screen, a listing display of red color detection bars, a listing display of average color bars, a listing display of thumbnails extracted as observation targets, a digest listing display of thumbnails extracted from a database based on a predetermined reference, and a diagnostic report are displayed at the bottom of the screen in addition to the display of a case data listing display window in which a case data number in a case data number field, and data such as the name and the ID of a patient, an examination date, etc. in an identification data field are displayed to be scrollable.

18 Claims, 9 Drawing Sheets

FOREIGN PATENT DOCUMENTS

| | | |
|---|---|---|
| EP | 2 156 784 A1 | 2/2010 |
| JP | 10-337274 | 12/1998 |
| JP | 2001-111992 | 4/2001 |
| JP | 2004-337596 | 12/2004 |
| JP | 2005-157227 | 6/2005 |
| JP | 2005-218584 | 8/2005 |
| JP | 2006-006915 | 1/2006 |
| JP | 2006-061626 | 3/2006 |
| JP | 2006-301535 | 11/2006 |
| JP | 2006-302043 | 11/2006 |
| JP | 2007-75155 | 3/2007 |
| WO | WO 2005/041763 A1 | 5/2005 |
| WO | WO 2006/109676 A1 | 10/2006 |
| WO | WO 2007/029819 A1 | 3/2007 |

OTHER PUBLICATIONS

International Preliminary Report on Patentability together with the Written Opinion dated Jan. 21, 2010.

Extended Supplementary European Search Report dated May 16, 2012 from related EP 08764201.3-2319.

* cited by examiner

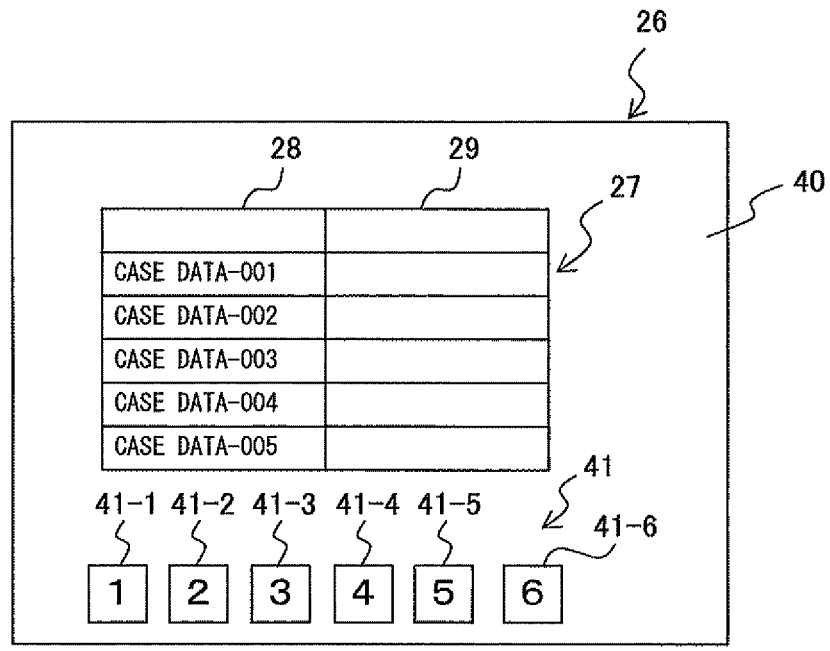
F I G. 4

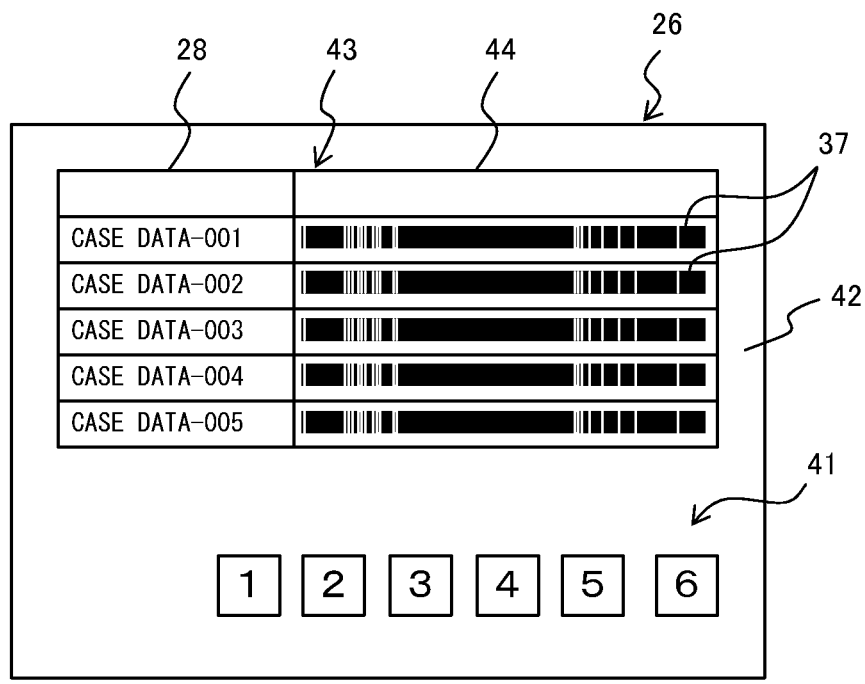
F I G. 5

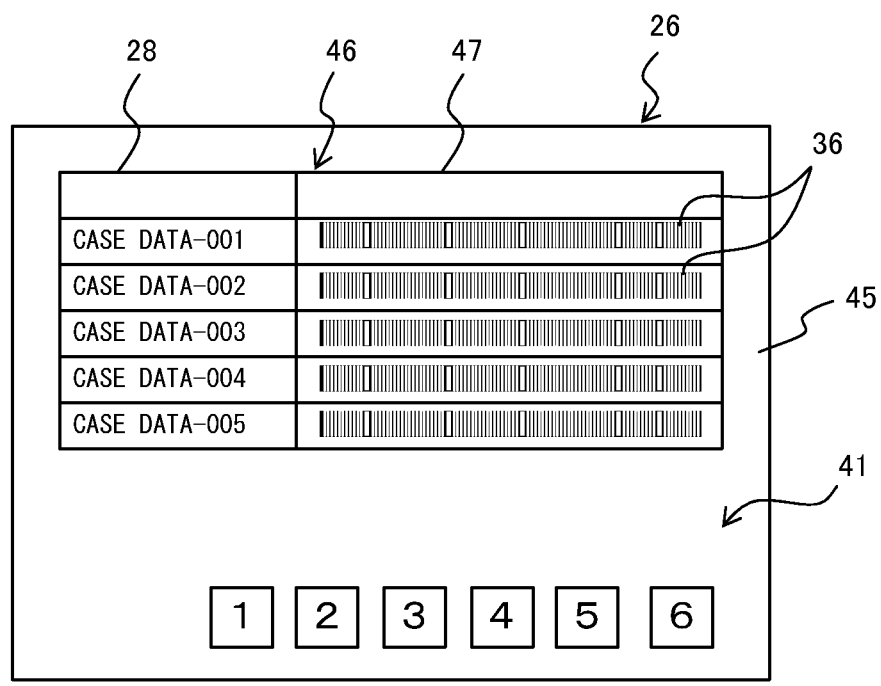
F I G. 6

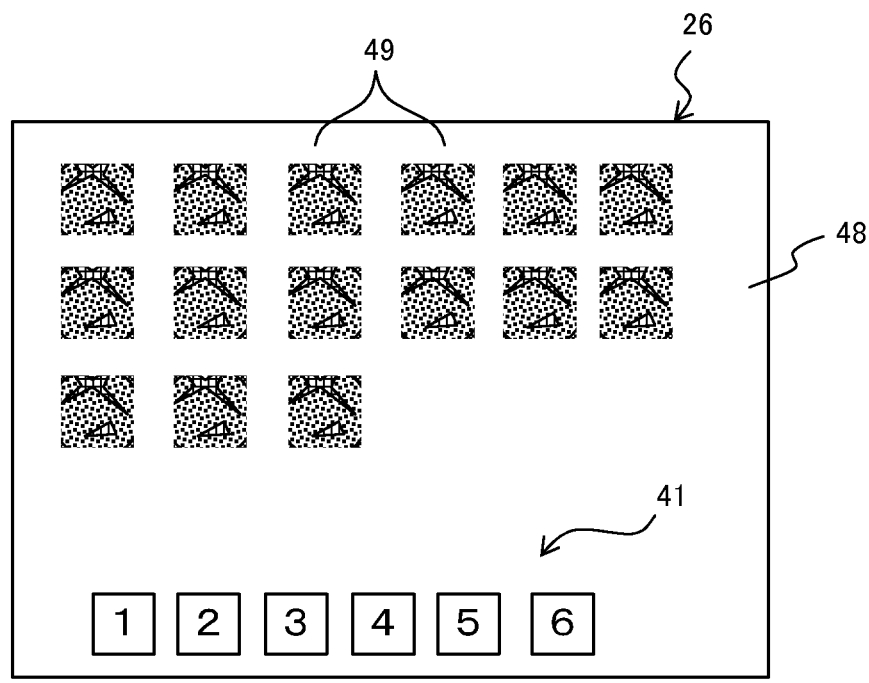
F I G. 7

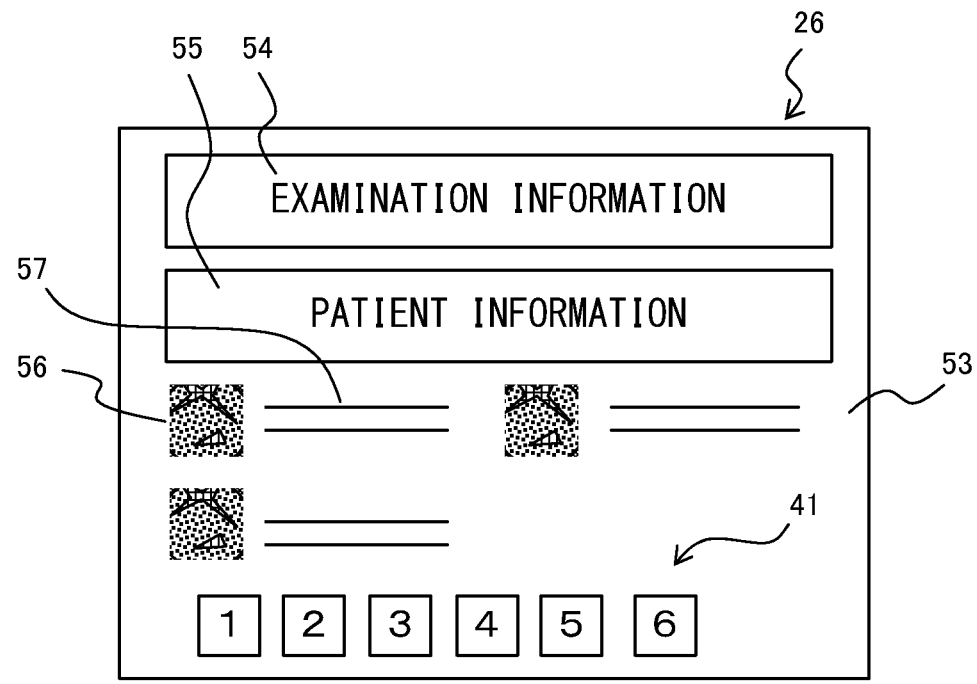
F I G. 9

DISPLAY PROCESSING APPARATUS FOR IMAGE INFORMATION

CROSS REFERENCE TO RELATED APPLICATION

This application is based upon and claims the benefit of priority from the prior Japanese Application No. 2007-169684 filed Jun. 27, 2007, the entire contents of which are incorporated herein by reference.

BACKGROUND OF THE INVENTION

1. Field of the Invention

The present invention relates to an image information display processing apparatus for executing a display process for a plurality of pieces of image information obtained by being captured with the elapse of time, for example, with a capsule endoscope that autonomously or heteronomously moves within a body to be examined.

2. Description of the Related Art

In recent years, a so-called swallow-type capsule endoscope has been made its debut in an endoscope field as disclosed, for example, by US Patent Application Publication No. 2002/0177779A1.

The capsule endoscope has an image capturing function and a wireless communication function. The capsule endoscope sequentially captures the images of organs such as the stomach, the small intestine, etc., and wirelessly transmits information about the sequentially captured images (electronic data representing images) during an observation period from when it is swallowed from the mouth of a patient in order to observe or examine the organs until when it is naturally excreted from the body.

The wirelessly transmitted image information in this way is received by a receiver that is provided outside the body of the patient, stored in a predetermined memory, and read and displayed on a display unit as occasion demands, whereby the image information becomes available for a diagnosis, etc. made by a doctor as disclosed, for example, by Japanese Published Unexamined Patent Application No. 2005-218584.

However, for such a capsule endoscope, the period from when it is swallowed from the mouth of a patient until when it is naturally excreted is an observation period or an examination period unlike a normal endoscope.

Case data shot with the capsule endoscope during this period is composed of approximately 60,000 images as materials shot for the maximum of approximately eight hours, and the number of pieces of image information (case data) is vast.

In addition, information about images shot with the capsule endoscope in the past include image information of many patients, and also information about images shot on different examination dates even for the same patient, and are stored in a database.

SUMMARY OF THE INVENTION

A display processing apparatus according to the present invention is a display processing apparatus for storing an image within a body to be examined, which is shot with an image capturing device introduced into the body to be examined, and for displaying the image on a display screen, and comprises a display unit having a case data display region for displaying on the display screen one or more pieces of case data including at least one of the ID of a patient, the name of the patient, and an examination date, and a case data associated information display region for displaying information associated with each piece of the case data, and a case data associated information display switching unit for switching the information associated with each piece of the case data displayed in the case data associated information display region.

BRIEF DESCRIPTION OF THE DRAWINGS

FIG. 4 is a schematic diagram showing an example of a case data listing display made on a display screen of a monitor device of a workstation in a capsule endoscope image filing system according to a second preferred embodiment of the present invention;

FIG. 5 is a schematic diagram showing an example of a listing display screen of red color detection bars for the respective pieces of case data, which is displayed on the display screen of the monitor device of the workstation in the second preferred embodiment;

FIG. 6 is a schematic diagram showing an example of a listing display screen of average color bars for the respective pieces of case data, which is displayed on the display screen of the monitor device of the workstation in the second preferred embodiment;

FIG. 7 is a schematic diagram showing an example of a listing display screen of thumbnails that are extracted beforehand for an observation and correspond to desired case data, which is displayed on the display screen of the monitor device of the workstation in the second preferred embodiment;

FIG. 9 is a schematic diagram showing an example of a diagnostic report display screen corresponding to desired case data, which is displayed on the display screen of the monitor device of the workstation in the second preferred embodiment.

DESCRIPTION OF THE PREFERRED EMBODIMENTS

Preferred embodiments according to the present invention are described in detail below with reference to the drawings.

Figure 1:
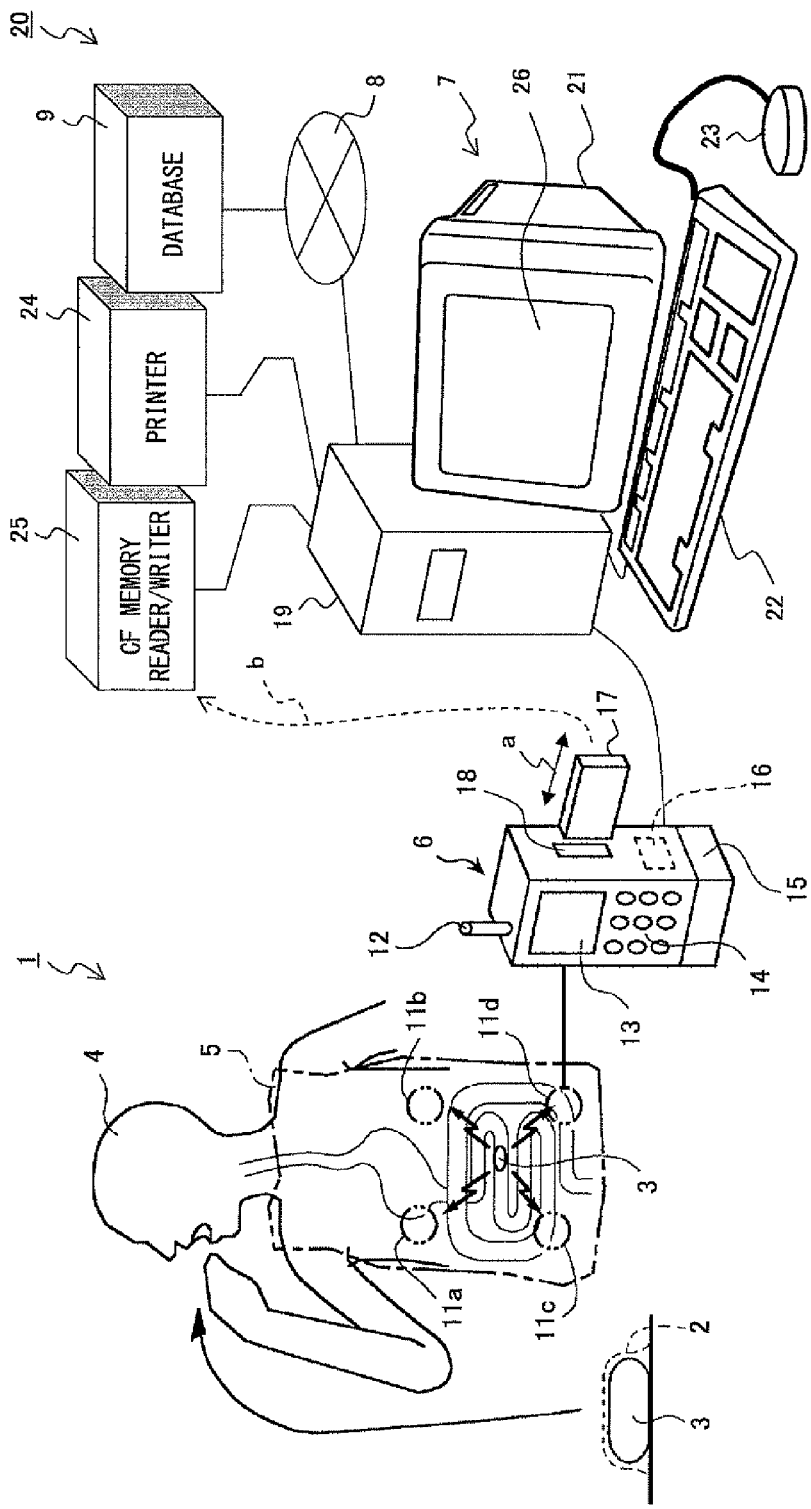
FIG. 1 is a schematic diagram showing the outline of a configuration of a capsule endoscope image filing system according to the present invention.

FIG. 1 is a schematic diagram showing the outline of a configuration of a capsule endoscope system according to the present invention, and a capsule endoscope image filing system included by the capsule endoscope system.

As shown in FIG. 1, the capsule endoscope system 1 according to this preferred embodiment is composed of a capsule endoscope 3 contained in a package 2, a patient who swallows the capsule endoscope 3 taken out of the package 2, namely, a person to be examined 4, a jacket 5 worn by the person to be examined 4, and a receiver 6 attachable/detachable to/from the jacket 5.

The capsule endoscope image filing system 20 is composed of a workstation 7 for executing processes such as storing, editing, etc. image data received by the receiver 6, and a database 9 connected to the workstation 7 via a network 8. The database 9 may be incorporated in the workstation 7.

An image capturing unit, a wireless unit, and a power supply are provided within the capsule endoscope 3. The capsule endoscope 3 wirelessly transmits image data, which is obtained by sequentially capturing the images of digestive organs such as the esophagus, the stomach, the small intestine, the large intestine, etc. with the image capturing unit with the elapse of time, as radio waves from the wireless unit to the outside during a period from when it is swallowed from the mouth of the person to be examined 4 in order to observe or examine the digestive organs until when it is excreted from the body.

The jacket 5 worn by the person to be examined 4 is equipped with a plurality (four in this figure) of antennas 11 (11a, 11b, 11c, 11d) that receive the radio waves of image data transmitted from the wireless unit of the capsule endoscope 3. These antennas 11 can make a wireless or wired communication with the receiver 6.

The number of the antennas 11 is not limited to four. The number may be a suitable number. Namely, the number may be any number as far as transmitted radio waves according to the position of the moving capsule endoscope 3 can be satisfactorily received.

On the outer surfaces of the receiver 6, an antenna 12 used to receive image data from the jacket 5 with radio waves via the antennas 11, a display unit 13 for displaying information required for an observation or an examination, and an inputting unit 14 for inputting information required for the observation or the examination are provided.

At the bottom of the receiver 6, a power supply unit 15 is provided to supply power also when the receiver 6 is carried. The power supply unit 15 is implemented, for example, with a dry battery, an Li ion secondary battery, an Ni hydride battery, etc (other types of batteries may be available as a matter of course).

Within the receiver 6, a signal processing/controlling unit 16 for executing processes required for an observation or an examination is provided, and also a slot 18 into/from which a CF (Compact Flash (registered trademark)) memory 17 for storing received image data is insertable/removable as indicated by a bidirectional arrow a shown in FIG. 1 is provided.

The workstation 7 is composed of a main body device 19, a monitor device 21 connected to the main body device 19, a keyboard 22, a mouse 23, etc. Additionally, the main body device 19 comprises various types of interfaces in addition to an interface for making a connection to the network 8 although these are not shown.

A printer 24, and a CF memory reader/writer 25 are connected to the workstation 7 in addition to the receiver 6 via the interfaces.

The workstation 7 has an image processing function with which a doctor or a nurse makes a diagnosis, etc. by displaying images within the digestive organs of the person to be examined 4, which are captured by the capsule endoscope 3, on the monitor device 21.

The doctor or the nurse can issue an instruction to capture the image data of body cavities of the person to be examined 4, which is transmitted from the capsule endoscope 3 and received by the receiver 6, from the receiver 6 while performing an input operation with the keyboard 22 or the mouse 23 on a man-machine interface displayed on the display screen 26 of the monitor device 21 of the workstation 7.

At this time, the image data can be directly captured from the receiver 6 wiredly, or can be captured from the CF memory 17 by inserting the CF memory 17 into the CF memory reader/writer 25 as indicated by an arrow b shown in FIG. 1.

Furthermore, the doctor or the nurse can issue instructions such as an instruction to store image data captured from the receiver 6 as described above, an instruction to call image data stored in the database 9 and to make an image data display to be described later on the display screen of the monitor device 21, an instruction to record diagnostic results obtained based on an observation of images to the database 9, and an instruction to print a carte, etc. with the printer 24.

The preferred embodiments according to the present invention are described by being specialized in the capsule endoscope system and the capsule endoscope image filing system. However, the present invention is not limited to these embodiments as a matter of course.

First Preferred Embodiment

Figure 2:
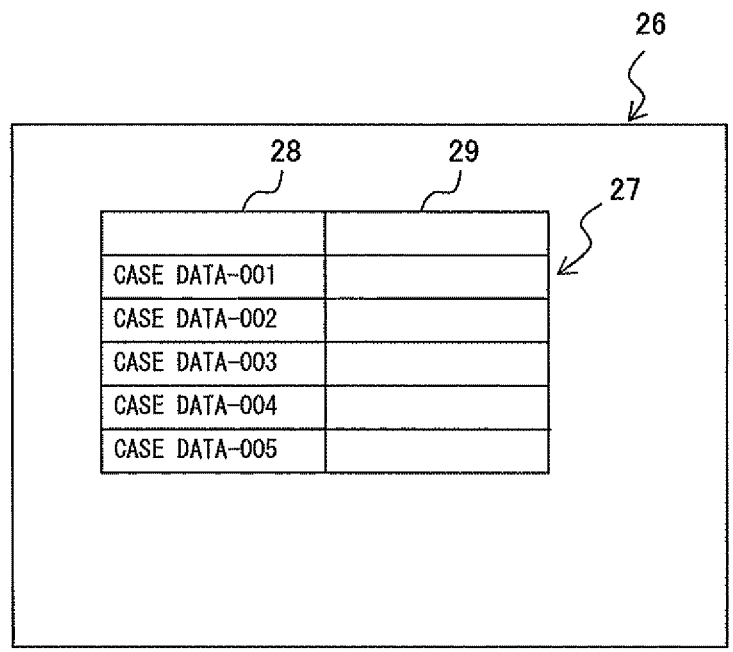
FIG. 2 is a schematic diagram showing an example of a case data listing display made on a display screen of a monitor device of a workstation in the capsule endoscope image filing system according to a first preferred embodiment of the present invention.

FIG. 2 is a schematic diagram showing an example of a case data listing display made on the display screen of the monitor device of the workstation in the capsule endoscope image filing system according to the first preferred embodiment of the present invention.

On the display screen 26 of the monitor device 21 of the workstation 7 shown in FIG. 1, a case data listing display window 27 is displayed with an initial operation procedure as shown in FIG. 2.

In the case data listing display window 27, case data numbers are displayed in an ascending order starting at 001 to 002, 003, . . . , in a case data number field 28 in the left portion. Additionally, identification data corresponding to each case data number in the left portion is displayed in an identification data field 29 in the right portion.

For example, at least the name and the ID of a patient, an examination date, etc. are displayed as the identification data displayed in the identification data field 29 although these are not shown in FIG. 2.

In FIG. 2, only five data rows are displayed in the case data number field 28 and the identification data field 29. However, all of data rows stored in the database 9 can be displayed with scrolling.

If the doctor or the nurse desires to obtain the case data of a desired examination date of a desired patient while he or she is viewing the identification data displayed in the identification data field 29, he or she selects the corresponding case data number, and performs an input operation, for example, double-clicks on the corresponding number with a pointing device such as the mouse, etc., so that an observation image screen is displayed.

Figure 3:
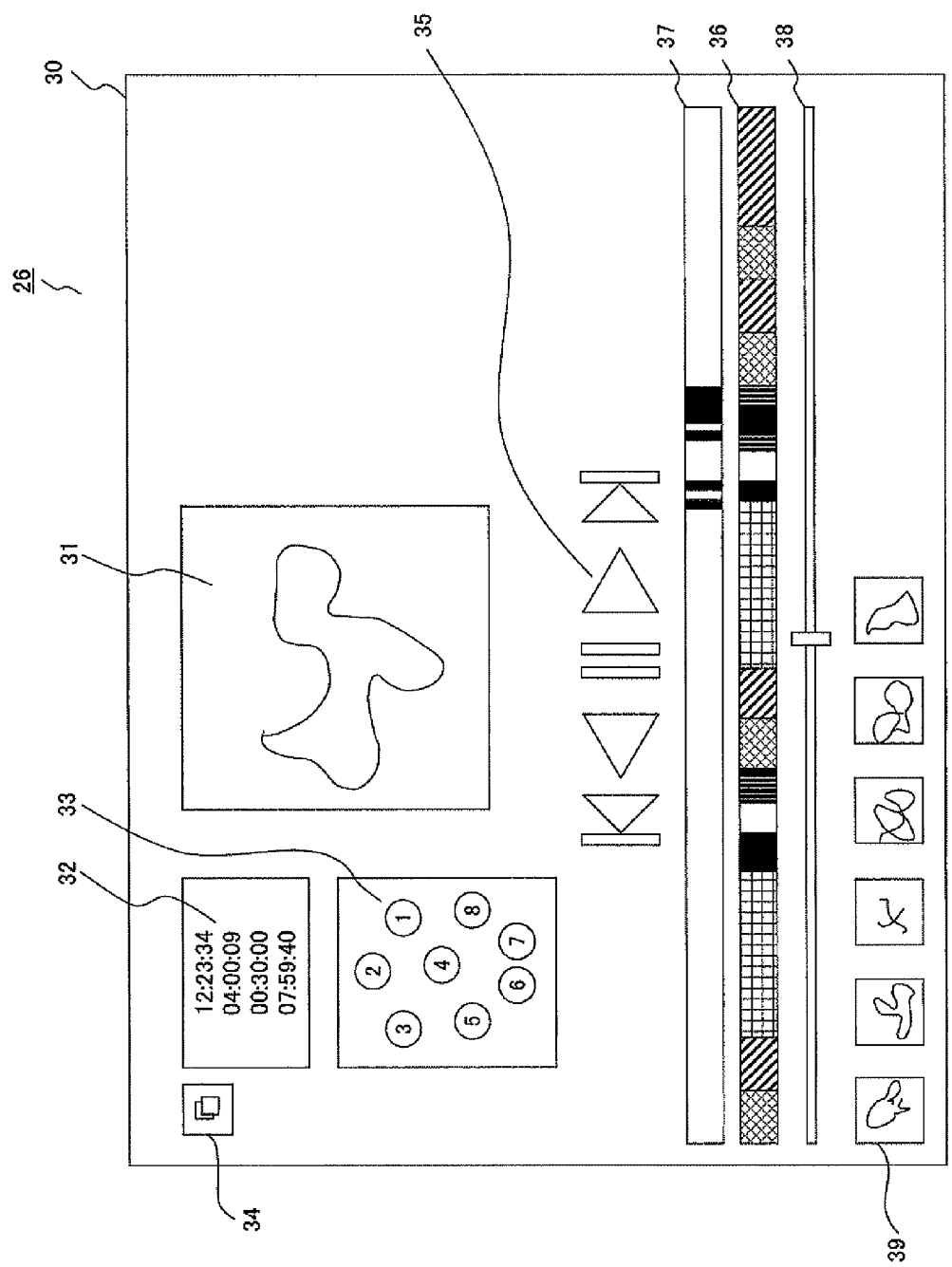
FIG. 3 is a schematic diagram showing an example of an observation image display screen displayed on the display screen of the monitor device of the workstation in the first preferred embodiment.

FIG. 3 is a schematic diagram showing an example of an observation image display screen displayed on the display screen of the monitor device of the workstation in the first preferred embodiment.

As shown in this figure, the currently selected observation image 31 is displayed in an upper middle portion of the observation image screen 30 displayed on the display screen 26. Four types of time data 32 associated with captured images are displayed in an upper portion at the left of the observation image 31, and image captured positions (positions within the body) data 32 is two-dimensionally displayed below the time data 32.

Additionally, a plurality (five in this figure) of instruction buttons 34 are displayed in an upper left portion of the display screen 26. Moreover, a replay button group 35 including replay buttons that are positioned on the right side of a stop button as a center and intended to respectively instruct a replay, a fast-forward replay and a frame-by-frame forward replay, and replay buttons that are positioned on the left side of the stop button and intended to respectively instruct a backward replay, a fast-backward replay and a frame-by-frame backward replay is displayed below the middle of the display screen 26.

Furthermore, a red color detection bar 37 and a time bar 38 are displayed above and below an average color bar 36 in a portion below the replay button group 35 on the display screen 26.

The average color bar 36 represents average colors of captured images in positions on the time axis while the capsule endoscope 3 is moving within the organs.

A display controlling unit controls the representation of average colors to be displayed as one horizontal average color bar 36 implemented by arranging vertical lines each of which is represented with an average color calculated for each captured image (video image) or for every plural images along the time axis of the time bar 38, namely, in time series in the horizontal direction of the display screen 26 in order to obtain image capturing positions by using a characteristic such that colors differ depending on the organs.

Horizontal lines each represented with an average color may be arranged in the vertical direction or an oblique direction in time series. Namely, the direction of the average color bar does not matter.

In the meantime, the display controlling unit controls the display of the red color detection bar 37 so that a position (red color detection position) at which bleeding is found on the time axis is represented as a red color line within the horizontal bar on the display screen 26.

The red color detection bar 37 is one type of lesion color bars. The red color detection bar 37 may be represented as a vertical or an oblique bar on the display screen. The direction of the red color detection bar does not matter.

A lesion is not limited to bleeding. There are other lesions that can be clearly identified with an image shot by the capsule endoscope 3. These lesions can be displayed with lesion color bars in blue, white or other colors other than the red color depending on lesions.

The present invention is described by using the red color detection bar as an example of a lesion color bar. Moreover, in FIG. 3, the time bar 38 is a bar that indicates the elapse of time during which the capsule endoscope 3 moves within the body of the person to be examined 4, and comprises a slide button.

By moving the slide button along the time bar 38 with a pointing device such as the mouse, etc., a captured image on the time axis specified with the slide button is displayed as the currently selected observation image 31.

Additionally, horizontally scrollable thumbnails 39 are displayed at the bottom of the display screen 26.

Unless otherwise specified, the currently selected observation image 31 among the thumbnails 39 is displayed at the center, and the thumbnails 39 of the captured images consecutive to the currently selected observation image 31 in time series are displayed at the right and the left of the currently selected observation image 31.

Alternatively, thumbnails of captured images that are sampled at predetermined time intervals or every predetermined number of thumbnails can be displayed.

Additionally, the doctor presses any of the instruction buttons 34 on the observation image screen 30 shown in FIG. 3, whereby, for example, a listing display of red color detection bars 37 for the respective pieces of case data shown in FIG. 2 can be made.

Furthermore, if the doctor desires to observe, for example, a listing display of average color bars 36 for the respective pieces of case data shown in FIG. 2 when observing the listing display of red color detection bars 37, he or she once restores the display to the observation image screen 30 shown in FIG. 3.

Then, the listing display of average color bars 36 for the respective pieces of case data shown in FIG. 2 can be made with the press of the instruction button 34 for instructing the listing display of average color bars 36.

Additionally, if the doctor desires to view a listing of thumbnails of image information that the doctor himself or another doctor, who previously operated the display processing apparatus, extracted as observation targets when the doctor observes the listing display of red color detection bars 37 or the listing display of average color bars 36 as described above, he or she once restores the display to the case data listing display 27 shown in FIG. 2, and selects desired case data.

Then, the doctor changes the display to the observation image screen 30 shown in FIG. 3, and presses the instruction button 34 for instructing the listing display of the thumbnails extracted as the observation targets, whereby the thumbnails of the image information extracted as the past observation targets are read from the database, and their listing display is made on the display screen 26.

Furthermore, if the doctor desires to observe a digest listing display of thumbnails corresponding to any piece of the case data when observing any of the above described display screens, he or she once restores the display to the case data listing display 27 shown in FIG. 2, and selects desired case data.

Thereafter, the doctor changes the display to the observation image screen 30 shown in FIG. 3. Then, the doctor presses the instruction button 34 for instructing the digest listing display of thumbnails, whereby the digest listing display of thumbnails corresponding to image information extracted from the database based on a predetermined reference can be made.

The predetermined reference may be predetermined time intervals such as 30-minute intervals, or every predetermined number of images such as every 4,000 images. Alternatively, the predetermined reference may be a reference for sampling one image each time the color tone of a shot image changes.

Furthermore, if the doctor desires to view a diagnostic report of examination results of a patient on one date when observing any of the above described display screens, he or she once restores the display to the case data listing display 27 shown in FIG. 2, and selects desired case data.

Then, the doctor changes the display to the observation image screen 30 shown in FIG. 3, and presses the instruction button 34 for instructing the display of the diagnostic report, whereby the diagnostic report corresponding to the selected case data is read from the database, and its data is displayed on the display screen 26.

Second Preferred Embodiment

As described above, the amount of image information intended for a diagnosis for respective pieces of case data stored in the database comes to a vast number of images such as approximately 60,000 images.

If operations such that the display is restored to the screen shown in FIG. 2 to select desired case data, and changed to the display screen shown in FIG. 3 to press any of the instruction buttons 34 are repeatedly performed every time an average color bar, a red color detection bar, a digest listing of thumbnails, a listing of thumbnails extracted as observation targets, or a diagnostic report is desired to be viewed, these operations can possibly require a lot more time to switch the screen and press the instruction buttons 34 than that to observe data.

Therefore, the present inventor devised display screens so that the above described screens can be displayed more quickly. This is described below as the second preferred embodiment.

FIG. 4 is a schematic diagram showing an example of a case data selection screen displayed on a display screen of a monitor device of a workstation in a capsule endoscope image filing system according to the second preferred embodiment of the present invention.

As shown in this figure, a case data listing display is made with a case data number field 28 and an identification data field 29 on the case data selection screen 40 according to the second preferred embodiment displayed on the display screen 26.

Six display call buttons 41 (41-1 to 41-6), which respectively correspond to various types of displays of image information of the case data displayed in the case data number field 28 and the identification data field 29, are displayed below the case data number field 28 and the identification data field 29.

The display call button 41-1 is a normal information display button for calling and displaying the case data selection screen 40 shown in FIG. 4 from other screens to be described later.

The display call button 41-2 is, for example, a red color detection bar display button for making a listing display of red color detection bars 37 for respective pieces of case data, which will be described later.

The display call button 41-3 is, for example, an average color bar display button for making a listing display of average color bars 36 for respective pieces of case data, which will be described later.

The display call button 41-4 is, for example, a thumbnail listing display button for making a listing display of thumbnails extracted as observation targets for each piece of case data, which will be described later.

The display call button 41-5 is, for example, a digest listing display button for making a digest listing display of thumbnails of image information extracted based on a predetermined reference for each piece of case data, which will be described later.

The display call button 41-6 is, for example, a report display button for displaying the data of a diagnostic report of each piece of case data, which will be described later.

These display call buttons 41 (41-1 to 41-6) are not limited to displayed buttons, and (their corresponding displays?) may be selected, for example, from a pull-down menu, or may be implemented as components selected with a pointing device such as the mouse, etc. on the screen. Alternatively, a display screen may be changed with the press of a numeric key 1, 2, . . . , or 6 on the keyboard 22 in a similar manner as in the case of selecting and pressing the display call buttons 41.

FIG. 5 is a schematic diagram showing an example of a listing display screen of red color detection bars for respective pieces of case data, which is displayed on the display screen of the monitor device of the workstation with the press of the display call button 41-2 (red color detection bar display button) in the second preferred embodiment.

As shown in this figure, a red color detection bar listing display window 43 is displayed on the red color detection bar listing display screen 42 for the respective pieces of case data displayed on the display screen 26 of the monitor device 21, and a case data number field 28 similar to that shown in FIG. 4 is displayed in the left portion of the window.

Additionally, red color detection bars 37 corresponding to the case data numbers in the case data number field 28 are respectively displayed in a bar display field 44 in the right portion of the window.

With this screen, whether the number of bleeding parts is either large or small (whether bleeding is either heavy or light?) can be visually grasped with ease for each piece of case data focused by a doctor who is operating the workstation. Moreover, for example, case data with a large number of bleeding parts can be visually grasped with ease from among many pieces of case data.

Furthermore, the display call buttons 41 (41-1 to 41-6) shown in FIG. 4 are displayed unchanged below the red color detection bar listing display window 43 on the red color detection bar listing display screen 42 shown in FIG. 5.

With these buttons, if a doctor who is operating/observing a screen desires to observe, for example, the average color bar of each piece of case data, he or she can immediately call a desired display screen from the red color detection bar listing display screen 42 shown in FIG. 5 without once restoring the display to the case data listing display window 27 shown in FIG. 2 to select the desired case data, and changing the display to the observation image screen 30 shown in FIG. 3 to press the instruction button 34.

Namely, the doctor presses the display call button 41-3 (average color bar display button) on the red color detection bar listing display screen 42 shown in FIG. 5, whereby the average color bar listing display screen is immediately displayed.

FIG. 6 is a schematic diagram showing an example of a listing display screen of average color bars for respective pieces of case data, which is displayed on the display screen of the monitor device of the workstation with the press of the display call button 41-3 (average color bar display button) in the second preferred embodiment.

As shown in FIG. 6, an average color bar listing display window 46 is displayed on the average color bar listing display screen 45 for the respective pieces of case data, which is displayed on the display screen 26 of the monitor device 21, and a case data number field 28 similar to that shown in FIG. 4 is displayed in the left portion of the window.

Additionally, average color bars 36 corresponding to the case data numbers in the case data number field 28 are respectively displayed in a bar display field 47 in the right portion of the window.

This screen makes it easy for a doctor who is operating the workstation to visually grasp the entire characteristic of each piece of case data at a glance.

The display call buttons 41 (41-1 to 41-6) shown in FIG. 4 are displayed unchanged below the average color bar listing display window 46 also on the average color bar listing display screen 45 shown in FIG. 6.

With these buttons 41, if a doctor who is operating/observing the screen desires to observe, for example, a listing display of thumbnails of image information that a doctor who previously operated the display processing apparatus extracted as observation targets, he or she can immediately call a desired display screen from the average color bar listing display screen 45 shown in FIG. 6 without once restoring the display to the case data listing display window 27 shown in FIG. 2 to select case data, and changing the display to the observation image screen 30 shown in FIG. 3 to press the instruction button 34.

Namely, the doctor presses the display call button 41-4 (thumbnail listing display button) after selecting desired case data on the average color bar listing display screen 45 shown in FIG. 6, whereby the listing display screen of thumbnails corresponding to the desired case data is immediately displayed.

The average color bar 36, the red color detection bar 37, and the lesion color bar are not limited to these shapes. They may take shapes that are respectively made to correspond to a frame bar indicating a sequence of frames. Alternatively, they may take shapes that are made to correspond to the time bar 38 or the frame bar, and their information to be displayed may be represented with a mark, an icon, an arrow, etc.

FIG. 7 is a schematic diagram showing an example of the listing display screen of thumbnails that are extracted beforehand for an observation and correspond to desired case data, which is displayed on the display screen of the monitor device of the workstation with the press of the display call button 41-4 (thumbnail listing display button), in the second preferred embodiment.

As shown in this figure, a listing display of thumbnails 49 of image information that a doctor who previously operated the display processing apparatus extracted as observation targets is made on the thumbnail listing display screen 48 displayed on the display screen 26 of the monitor device 21.

This screen enables a doctor who is operating the workstation to verify the images that a medical staff member previously extracted as observation targets for the case focused by the doctor, and to visually grasp the case based on the thumbnails.

The display call buttons 41 (41-1 to 41-6) shown in FIG. 4 are displayed unchanged below the listing display region of the thumbnails 49 also on the thumbnail listing display screen 48 shown in FIG. 7.

Accordingly, the doctor who is operating/observing the screen does not need to once restore the display to the case data listing display window 27 shown in FIG. 2 to select case data, and to change the display to the observation image screen 30 shown in FIG. 3 to press the instruction button 34, if he or she desires to observe, for example, a digest listing display of thumbnails corresponding to the case data the thumbnail listing display of which is currently observed by the doctor.

Namely, on the thumbnail listing display screen 48 shown in FIG. 7, the thumbnail digest listing display screen corresponding to the case data currently being observed is immediately displayed with the press of the display call button 41-5 (thumbnail digest listing display button) on the thumbnail listing display screen 48 shown in FIG. 7.

There is no need to restore the display to the case data listing display window 27 shown in FIG. 2 even if not the thumbnail digest listing display corresponding to the case data currently being observed but a thumbnail digest listing display corresponding to another piece of case data is desired to be viewed.

Namely, in this case, it is only necessary that the case data listing display screen 40 shown in FIG. 4 is displayed with the press of the display call button 41-1 (normal information display button) on the thumbnail listing display screen 48 shown in FIG. 7 to select a desired case data number, and the display call button 41-5 (thumbnail digest listing display button) displayed on the listing display screen 40 of the corresponding case data is pressed.

Figure 8:
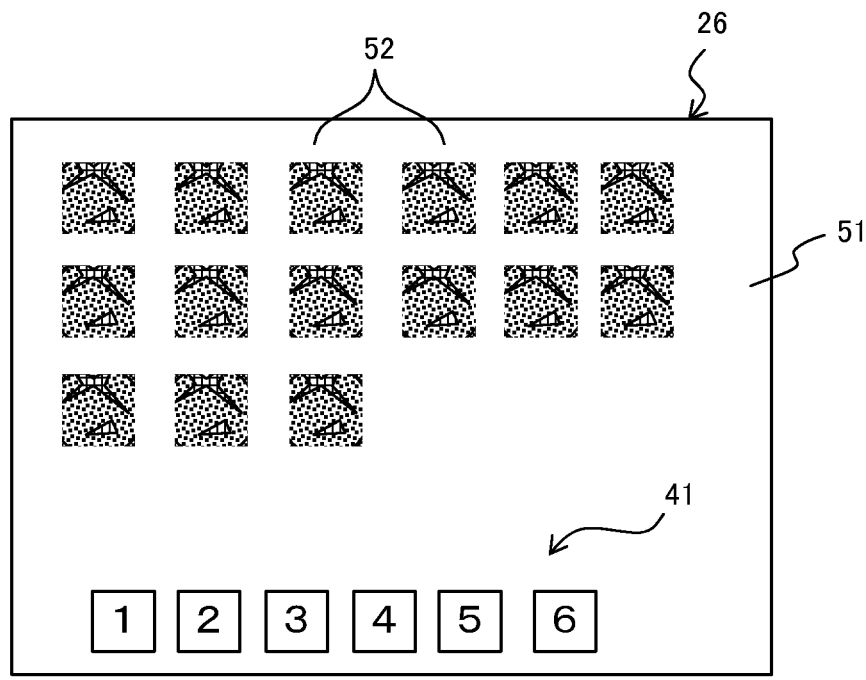
FIG. 8 is a schematic diagram showing an example of a digest listing display screen of thumbnails corresponding to desired case data, which is displayed on the display screen of the monitor device of the workstation in the second preferred embodiment.

FIG. 8 is a schematic diagram showing an example of a digest listing display screen of thumbnails corresponding to desired case data, which is displayed on the display screen of the monitor device of the workstation with the press of the display call button 41-5 (thumbnail digest listing display button), in the second preferred embodiment.

As shown in this figure, a listing display of thumbnails 52 of captured images, which are sampled based on a predetermined reference (predetermined time intervals, every predetermined number of images, or each time a color tone changes), is made on the thumbnail digest listing display screen 51 displayed on the display screen 26 of the monitor device 21.

With the digest listing display of thumbnails, thumbnails may be displayed not only as a listing of still images but also as moving images in time series.

In either case, a doctor or a nurse can grasp representative images extracted from the entire case data, and can select case data based on the results.

The display call buttons 41 (41-1 to 41-6) shown in FIG. 4 are displayed unchanged below the digest listing display region of the thumbnails 52 also on the thumbnail digest listing display screen 51 shown in FIG. 8.

Accordingly, if a doctor who is operating/observing the screen desires to view, for example, a diagnostic report including patient information, examination information, an extracted thumbnail, note information of a thumbnail, and the like corresponding to the case data the thumbnail digest listing display of which is currently observed by the doctor, he or she can immediately display the diagnostic report corresponding to the case data currently being observed with the press of the display call button 41-6 (report display button) on the screen shown in FIG. 8 without restoring the display to the case data listing display window 27 shown in FIG. 27, and changing the display to the observation image screen 30 shown in FIG. 3.

FIG. 9 is a schematic diagram showing an example of a diagnostic report display screen corresponding to desired case data, which is displayed on the display screen of the monitor device of the workstation with the press of the display call button 41-6 (report display button), in the second preferred embodiment.

As shown in this figure, on the diagnostic report display screen 53 displayed on the display screen 26 of the monitor device 21, examination information such as an examination date, the number of effective captured images, and the like are displayed in an examination information display region 54 at the top of the diagnostic report display screen 53, and patient information such as the name and the ID, etc. of a patient are displayed in a patient information display region 55 below the examination information display region 54.

Additionally, thumbnails 56, and a report field 57 that describes a report of a symptom indicated by each thumbnail 56 are displayed below the patient information display region 55. Additionally, the display call buttons 41 (41-1 to 41-6) shown in FIG. 4 are displayed unchanged also at the bottom of the screen.

The diagnostic report display screen 53 enables a doctor or a nurse to select case data after verifying diagnoses previously made.

As described above, the average color bar, the red color detection bar, a listing of extracted thumbnails, a digest listing of thumbnails, or a diagnostic report can be immediately verified with the press of any of the display call buttons 41 (41-1 to 41-6) on the case data selection screen 40 shown in FIG. 4.

As a result, an image representing each characteristic can be quickly called and displayed on the monitor device, and can be visually identified unlike the conventional technology for identifying a case based on only character information such as the ID and the name of a patient, an examination date, etc. and for selecting case data.

Namely, the characteristic of each case, for example, a case with a characteristic of a lot of bleeding can be quickly identified on the case data selection screen 40.

Additionally, the display call buttons 41 (41-1 to 41-6) are displayed on all of the above described screens, whereby a desired screen can be called with a single operation not only from the case data selection screen 40 but also from any of the screens. As a result, case data can be identified in various terms, and data can be quickly selected.

Note that the red color detection bar or the average color bar of case data may be displayed beforehand on the case data selection screen 40.

The present invention is not limited to the above described preferred embodiments, and can be practically modified in a variety of ways within a scope that does not depart from the scope and the spirit of the present invention.

What is claimed is:

1. A display processing apparatus for storing an image within a body to be examined, which is captured with an image capturing device introduced into the body to be examined, and for displaying the image on a display screen, comprising:
 a display unit having a listing display region on the display screen for displaying a plurality of lists of case data, and a display region which displays each of the case data in the listing display region, the display region comprising:
  a case data number display region for displaying the case data number, and
  a case data associated information display region for displaying case data associated information associated with each piece of the case data;
 a switching instruction unit for instructing display processing apparatus to switch the case data associated information displayed in the case data associated information display region; and
 a display controlling unit equipped with a processor for controlling to switch the display of information displayed on the case data associated information display region, following the instruction by the switching instruction unit, to either an image summarizing information of image information included in each piece of the case data, or information which includes at least one of an ID of a patient, a name of the patient, and an examination date for each piece of the case data.

2. The display processing apparatus according to claim 1, wherein the information associated with each piece of the case data is an entire average color bar configured by arranging in time series average colors each calculated for every one or more images among images within the body to be examined on the display screen.

3. The display processing apparatus according to claim 1, wherein the information associated with each piece of the case data is an entire lesion color detection bar configured by arranging in time series colors according to lesions respectively for images within the body to be examined on the display screen.

4. The display processing apparatus according to claim 1, wherein the information associated with each piece of the case data is a listing of thumbnails of images extracted from among images within the body to be examined based on a predetermined reference.

5. The display processing apparatus according to claim 1, wherein the information associated with each piece of the case data is a moving image configured with images extracted from among images within the body to be examined based on a predetermined reference.

6. The display processing apparatus according to claim 1, wherein the information associated with each piece of the case data is a listing of thumbnails that a medical staff member selects as observation targets.

7. The display processing apparatus according to claim 1, wherein the information associated with each piece of the case data is a moving image configured with images that a medical staff member selects as observation targets.

8. The display processing apparatus according to claim 1, wherein the information associated with each piece of the case data is a diagnostic report including at least one of patient information, examination information, an extracted thumbnail, and note information of the extracted thumbnail.

9. The display processing apparatus according to claim 4, wherein the predetermined reference is a reference of whether or not a predetermined amount of time elapses from a preceding extracted image.

10. The display processing apparatus according to claim 4, wherein the predetermined reference is a reference of whether or not a predetermined number of images are shot from a preceding extracted image.

11. The display processing apparatus according to claim 4, wherein the predetermined reference is a reference of whether or not a lesion is detected from an image as an observation target.

12. The display processing apparatus according to claim 4, wherein the predetermined reference is a reference of each color tone change.

13. The display processing apparatus according to claim 1, wherein said case data associated information display switching unit operates a component displayed on the display screen with a press of a mouse.

14. The display processing apparatus according to claim 13, wherein the component displayed on the display screen is any of a display switching button and a pull-down menu.

15. The display processing apparatus according to claim 1, wherein said case data associated information display switching unit is a key operation performed on a keyboard, to which a particular operation is assigned.

16. The display processing apparatus according to claim 1, wherein said case data associated information display switching unit is continually displayed and ready for accepting an input while one or more pieces of case data are displayed.

17. A display processing apparatus according to claim 1, wherein the display controlling unit makes a listing display in a state where the case data display region and the image extracted information are arranged for each piece of the case data.

18. A display processing apparatus according to claim 1, wherein the display controlling unit makes a listing display in a state where the case data display region and the image extracted information are in a row.

* * * * *